United States Patent [19]

Halaka

[11] Patent Number: 5,581,349
[45] Date of Patent: Dec. 3, 1996

[54] METHOD FOR BIOLOGICAL CELL AND PARTICULATE ANALYSIS

[76] Inventor: Folim G. Halaka, 42 S. Lewis Rd., Waukegan, Ill. 60085

[21] Appl. No.: 411,276

[22] Filed: Mar. 27, 1995

[51] Int. Cl.$^6$ ................................................. G01N 15/02
[52] U.S. Cl. ..................... 356/336; 356/338; 356/244; 356/440; 250/222.2; 250/574
[58] Field of Search ................................ 356/336, 338, 356/344, 244, 440; 364/555; 204/180.1

[56] References Cited

U.S. PATENT DOCUMENTS

| | | | |
|---|---|---|---|
| 3,870,612 | 3/1975 | Flygare et al. | 204/180 R |
| 4,233,664 | 11/1980 | Grandclamp | 364/555 |
| 5,298,967 | 3/1994 | Wells | 356/336 |

OTHER PUBLICATIONS

Kenneth S. Schmitz, Dept. of Chemistry, U of MO–Kansas City Article from Chemical Physics Letters, vol. 63, No. 2, May 15, 1979 titled "Quasielastic Light Scattering by Biopolymers, Center of Mass Motion of DNA in the Presence of a sinusoidal electric field."

B. R. Ware, Dept of Chemistry, Harvard University, article from Advances in Colloid and Interface Science, titled "Electrophoretic Light Scattering".

Primary Examiner—Frank Gonzalez
Assistant Examiner—Reginald A. Ratliff
Attorney, Agent, or Firm—Paul M. Denk

[57] ABSTRACT

An analytical device for detecting and analyzing the population of neutral or electrically-charged solutes, including providing a light source for producing a collimated beam, providing a solution vessel containing the sample solution to be analyzed, directing the light beam through the sample solution to thereby produce scattered light, a photomultiplier or a photon counter for detecting the scattered light, said photomultiplier being positioned at an angle to receive the scattered light from the collimated beam, an analog-to-digital converter communicating with the photomultiplier, converting the electrical signals output into a digital output, a digital correlator for receiving the digital output and to calculate a time autocorrelation function of the motion of the solutes in the fluid medium, immersing two electrodes in the solution vessel, generating an electrical field between the two electrodes, positioning the electrodes such that a field gradient is created between the electrode, and such that the light beam partially impinges on one of the electrodes to create a heterodyne effect, and an electrical field generator connected to said electrodes, producing an oscillating electrical signals, that can polarize solutes in the solution, the electrical signal generated at a frequency of 0 to 1,000 million hertz.

16 Claims, 6 Drawing Sheets

METHOD FOR BIOLOGICAL CELL AND PARTICULATE ANALYSIS

BACKGROUND OF THE APPLICATION

This invention relates to an improved method for identifying polarizable particles, macromolecules, and biological cells and a device for carrying out the method.

Identification of molecules, particles, and biological cells constitutes a major part to their purification, utility, and production. Identifying components in solution is equally important for both the biotechnology and chemical industries. In the chemical polymerization to manufacture commercial polymers and latex particles, for example, knowledge and control of the distribution of particle growth and size are critical. The situation is at least as complicated for biological organisms, where details about protein and cell populations are critical. The terms: particles, cells, macromolecules, particulates, and polymers are used here interchangeably, unless otherwise noted.

The present invention describes a device and a method for the identification of polarizable particles, macromolecules, and biological cells. The invention detects the behavior of dielectric materials in non-uniform fields. Dielectric properties are indicative of the polarizabilities of the macromolecules, cells, and particles. The detection of these properties is accomplished by measuring the modulation in the time autocorrelation function, measured by a technique such as dynamic light scattering, DLS. Current applications of DLS measure the Brownian (random) motion of molecules. Under the influence of a non-uniform electric field, polarizable macromolecules undergo characteristic motion, called dielectrophoresis. For the sake of clarity, a brief introduction to the basis of DLS and dielectrophoresis phenomena is presented below.

In a DLS experiment, a laser light impinges on a solution of macromolecules and the intensity of the scattered light is measured at an angle, $\theta$. A typical apparatus setup for DLS is presented in FIG. 1. The frequency of light is Doppler shifted due to the Brownian motion of the scattering macromolecules in the scattering volume, defined by the incident and scattered beam geometries at their intersection. The frequency shifts are related to the diffusion coefficients of the scattering species. Current DLS experiments measure the Fourier transform of these frequency shifts as the time autocorrelation function of the intensity fluctuations produced by molecular motion in solution. Time autocorrelation functions are exponential with time constants which are characteristic of the diffusion coefficients of the scattering species. From these coefficients, useful information can be obtained on the scattering molecules, primarily a measure of their size in solution. For a monodisperse system of particles, the heterodyne intensity autocorrelation function, $C(\tau)$, can be written as:

$$C(\tau) = <N^2>e^{-q^2D\tau}, \quad (1)$$

where $<N>$ is the average number of particles, $\tau$ is the delay time used to construct $C(\tau)$, and q is an experimental constant wherein:

$$q = \frac{4\Pi n}{\lambda} \sin\frac{\theta}{2}. \quad (2)$$

Here, n is the refractive index of the solution, $\lambda$ is the wavelength of light and $\theta$ is the scattering angle. In Equation (1), D is the diffusion coefficient, which for a spherical particle is:

$$D = \frac{kT}{6\Pi\eta r}, \quad (3)$$

where k is the Boltzmann constant, T is the absolute temperature, $\eta$ is the viscosity and r is the particle radius.

An analysis of the autocorrelation functions using Equations 1–3 can lead to the extraction of the diffusion coefficient of the scattering species and, hence, a measure of their size.

In polydisperse systems, the measured autocorrelation function is a sum of exponentials (or, for continuous distribution, an integral) representing the different species present, $$C(\tau) = \int G(\Gamma)e^{-\Gamma\tau}d\Gamma, \quad (4)$$

where $\Gamma$ is the exponent in Equation 1, (.i.e.$\Gamma = q^2 D$).

As Equation 4 shows, except for a single solute (monodisperse) systems, $C(\tau)$ data will be composed of a sum of exponentials. Analysis of multiple exponentials is difficult, even though clever methods have been developed for such analyses. The origin of the difficulty is that exponentials overlap quite strongly, with no discernible structure developed in the resulting functional form. The present invention, in addition to furnishing a new tool for the identification of macromolecules, also provides a guide to overcoming analysis difficulties by giving an estimate of the number of components present.

DIELECTROPHORESIS

The familiar phenomenon of electrophoresis results from the interaction of charged molecules and particles with an electric field. The field is usually uniform and causes a net translational motion of the particles. Neutral particles do not exhibit such an effect. The phenomenon of dielectrophoresis relates to the motion of particles in non-uniform (DC or oscillating) electric fields. This effect is exhibited by polarizable macromolecules, even if they are electrically neutral. When a particle or a macromolecule is polarizable, the field induces a polarization, or charge separation. It must be appreciated that there are various mechanisms for inducing polarization. In dielectrophoresis, the spatial non-uniformity of the field induces a directed motion toward maximum field intensity (positive dielectrophoresis). Positive dielectrophoresis occurs when the dielectric constant of the particle is larger than that of the medium (see Equation 6), while negative dielectrophoresis occurs when the particle dielectric constant is smaller. These effects are depicted schematically in FIG. 2. Hence, polarizable macromolecules, such as emulsions, suspensions and solutions of DNA and cells, will be affected by the field. Macromolecules can be characterized by their motion in response to the dielectrophoretic effect.

The force imposed by dielectrophoresis depends on several factors, including the oscillating electric field strength and its frequency, the dielectric constant and conductivity of the particle and the suspending medium, and the spatial configuration of the electrodes. This force, F, can be represented as:

$$F = Vg\nabla E^2 \quad (5)$$

where V accounts for the particle volume and $\nabla E^2$ is an expression of the effect of the electric field. It can be seen that the force imposed by dielectrophoresis depends on both field strength and on the field gradient, as $\nabla E^2$ may also be written as 2E∇E. g is a function that includes the properties of the particle and the medium which are relevant to the dielectrophoretic effect, namely their electrical permittivities:

$$g = g(e_m^*, e_p^*) = \frac{3}{4} e_m Re \frac{(e_p^* - e_m^*)}{(e_p^* + 2e_m^*)}, \quad (6)$$

Where $e^*_p$ and $e^*_m$ are the complex permittivities of the particle, p, and the medium, m The dielectric behavior of biopolymers and cells reflects several modes of polarizability. The different modes can be generalized as the polarization of water, dissolved biomolecules (proteins, sugars, DNA, etc.), charge rearrangement around a membrane, and most characteristically for cells, the action of the electrical double layer at the interface of cellular membranes where surface charges are localized. The last effect contributes a large magnitude to polarization, and is the explanation for the apparent extremely high values of dielectric constants observed for biological cell suspensions. The existence of the double layer in biological cells makes the cells particularly responsive to the effect of dielectrophoresis. Variations in the conditions listed above, and in particular the distribution of the membrane charges would lead to a change in the double layer and, hence, a discernible and unique response to the dielectrophoretic force.

The motion induced upon the macromolecules is peculiar to a particular population of macromolecules in solution. The importance of this motion in conjunction with the DLS is that the motion is non-random (unlike Brownian motion). As previously indicated, it is sensitive to the factors affecting the polarizability of the macromolecule to the dielectrophoretic effect is the charge distribution on the macromolecule. Changes in cell conditions, metabolism, or the infection of cells by invading microorganisms and viruses would change the charge distribution inside the cells and on their membranes. It is the premise of this invention that changes in cells which alters the cells charge distribution would manifest itself in the dielectrophoretic effect. The present invention presents a method to detect such changes.

PRIOR ART

DLS is a widely used technique. There are two techniques that use the more familiar effect of electrophoresis in conjunction with DLS. Electrophoretic light scattering has been demonstrated. The method uses electrophoresis to induce uniform motion, which modulates the time autocorrelation function and discriminates between molecules depending on their electrophoretic mobility. Since in electrophoresis only charged macromolecules would exhibit migration under the effect of the electric field, this technique is limited to detection of macromolecules which posses a net charge, and suffers the drawbacks of electrophoresis phenomenon, mainly heat generation, electronic polarization, and bubble formation due to electrolysis. This method has been used to characterize monomer and dimeric bovine serum albumin (BSA) in solution.

A low frequency field (frequencies <100 Hz) has also been used in a similar fashion to electrophoretic light scattering. The low oscillation field, called sinusoidal electric field (hence, DLS-SEF) was proposed to avoid some of the drawbacks in electrophoretic light scattering. The method has the advantages of reducing the Joules heating and the bubble formation as well as reducing the electrodic polarization encountered in the DC electrophoresis.

The present invention is phenomenologically different from the prior art. In electrophoretic light scattering, as well as DLS-SEF, the electrophoretic mobility is the discriminating factor. Both techniques are limited to charged molecules, and the limitations of electrophoresis. The discriminating factors in the present invention are the dielectric, or polarization properties.

SUMMARY OF THE INVENTION

The invention comprises a device which consists of a sample cell, electrodes for creating a field gradient, a source for creating oscillating electrical field with frequency in the radio frequency (RF) range, a light source (laser), optics for collimating and guiding of light beam, detection components, and data collection, storage, analysis and display components. The sample cell, depicted schematically in FIG. 3, contains the mixture of the macromolecules to be analyzed. Its walls must be transparent to light, and are made of glass or quartz. The cell may be immersed in a bath of index-matching fluid to minimize the scattering of the laser at the glass-air interface. The electrodes are comprised of noble metal, they may be shielded by a suitable insulator, leaving only the tips unshielded. The edge of one of the electrodes is displaced from the edge of the other electrode so as to create a non-uniform field. The electrodes are aligned so that a part of the incident light beam hits the tip of an electrode to create a heterodyne mode. The RF source provides the electric power needed for an electric field and field gradient generation. The light source provides a coherent (laser) beam at a wavelength suitable for the mixture to be analyzed, so that components in the mixture do not absorb the light and produce heat. The optics consist of lenses and mirrors to focus the beam into a small area in the sample cell and to convey the scattered light to the detection system. The detection system comprises of a photomultiplier tube or a photon counter, an analog-to-digital converter to convert the light pulses into digitized input, a correlator which uses the digitized input to calculate the time autocorrelation function, C(τ), which can be stored using a digital computer, and analyzed on-line. or thereafter.

The number of components in a mixture is analyzed by inducing directed (non-Brownian) motion in particles using an electric field gradient. This amounts to 'modulating' the exponential decay time of the Brownian motion measured in DLS experiments. The modulation imposes a sinusoidal component onto the exponentially decaying autocorrelation function of the form:

$$C'(\tau) = C(\tau) e^{-iq \cdot v\tau} \quad (7)$$

where C(τ) is the time autocorrelation function for the Brownian motion (Equations 1 or 4), $i = \sqrt{-1}$, and v is the instantaneous velocity of the particles undergoing directed motion under the applied external field in the scattering volume. The prime in C'(τ) indicates that a field is applied. If the imaginary part is ignored, equation 7 can be written as:

$$C'(\tau) = C(\tau) \cos(q \cdot v\tau), \quad (8)$$

Analysis of data may be performed by the Fourier transform after removal of the component of the spectrum due to the Brownian motion. To detect the number of components, or dispersions, in a system, each with its characteristic v, the Fourier transform of C'(τ) is performed and the number of peaks in the transform are related to the number of dispersions present. In addition to the determination of the number of components in the mixture from the peaks in the transform (v space), the peaks may be assigned to species present in the dispersion. Each peak in v space (spectrum) under normalized conditions of field strength and gradient would give a mobility characteristic of an individual population present. In this invention, these mobilities are called the dielectrophoretic mobilities.

Figure 8:
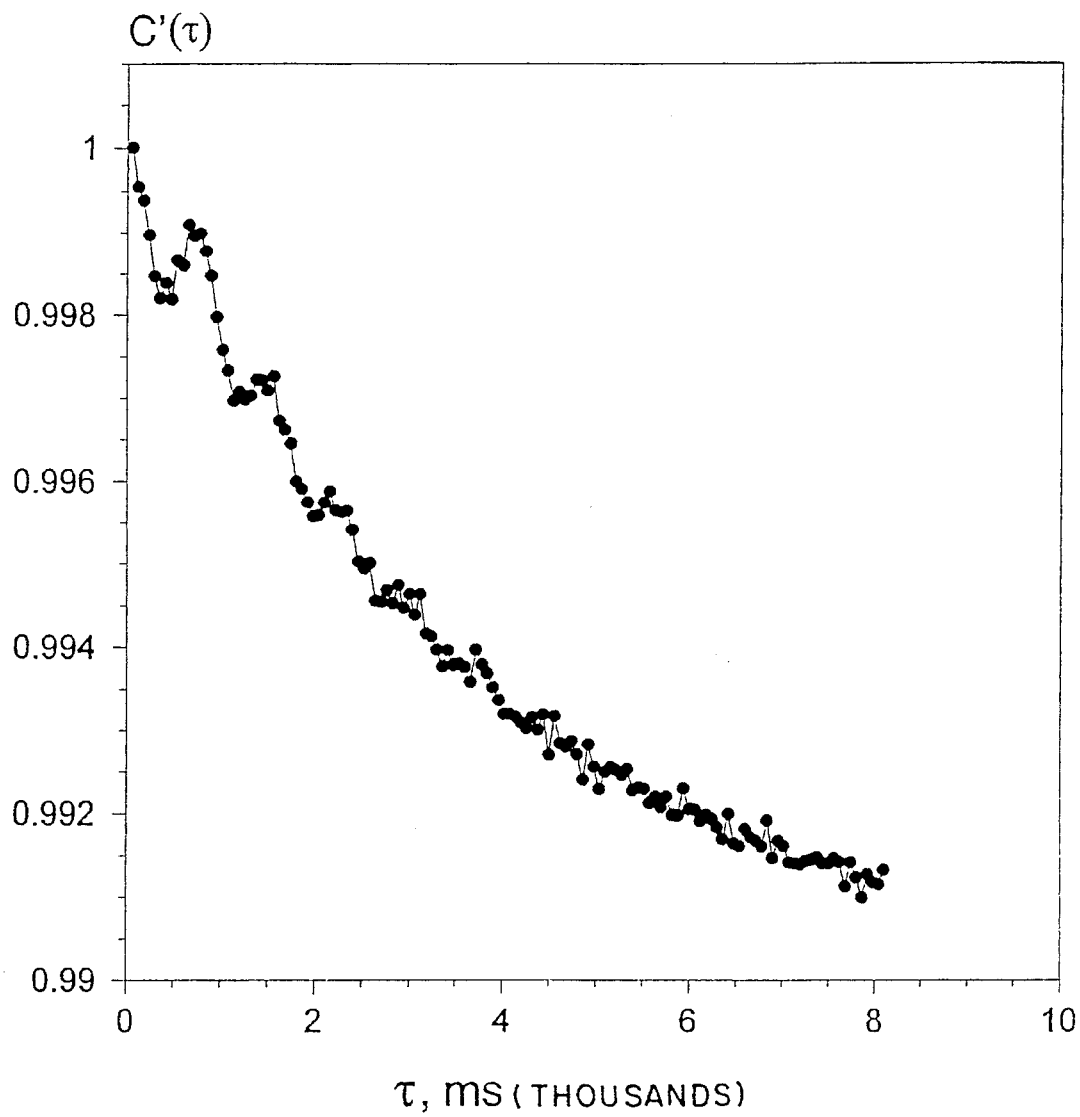
FIG. 8 is a graph similar to FIG. 5 for a Baker's yeast cell suspension.

FIG., 8A is a graph plotting the Fourier transform for the data of FIG. 8;

DESCRIPTION OF THE PREFERRED EMBODIMENTS

Figure 4:
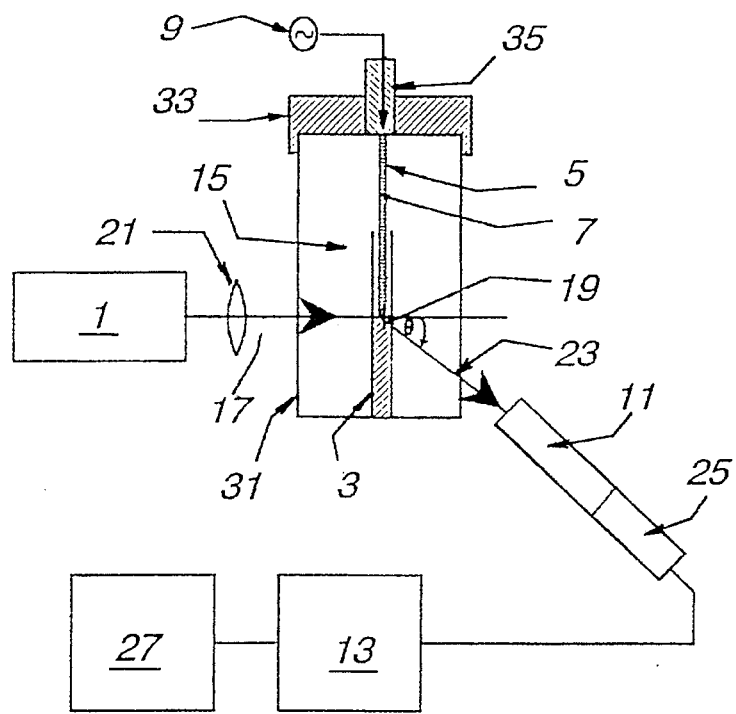
FIG. 4 is a diagram of a device used to carry out the identification of macromolecules and biological cells based on their dielectrical properties according to the present invention.

In referring to the drawings, and in particular FIG. 4, a schematic is shown of one illustrative embodiment of a device to carry out the identification of macromolecules and biological cells based on their dielectrical properties. The device includes a coherent light source (laser) 1, a sample cell 3 which contains the solution under study, platinum electrodes 5 and 7 for creating a field gradient, a source 9 for creating oscillating electrical field with frequency in the radio frequency (RF) range and an RF amplifier, if necessary, a detector or photomultiplier 11 positioned at a specified scattering angle, a digital correlator 13, and the associated electronics and controls normal to DLS measurements, such as those obtained from Brookhaven Co., of Holtsville, N.Y.

Figure 2A:
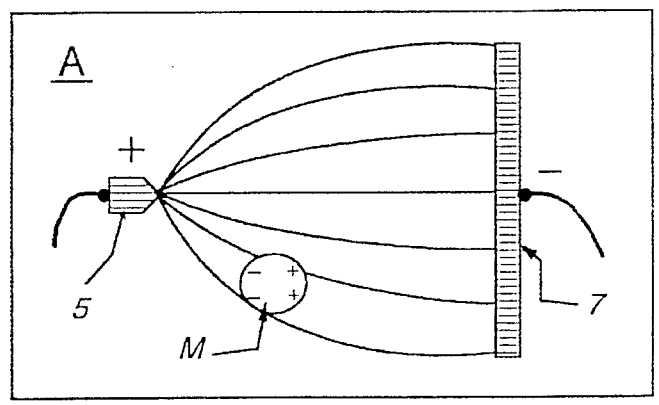
FIG. 2A is a schematic depiction of light scattering due to DLS performed in accordance with the present invention using the apparatus of FIG. 1.
Figure 2B:
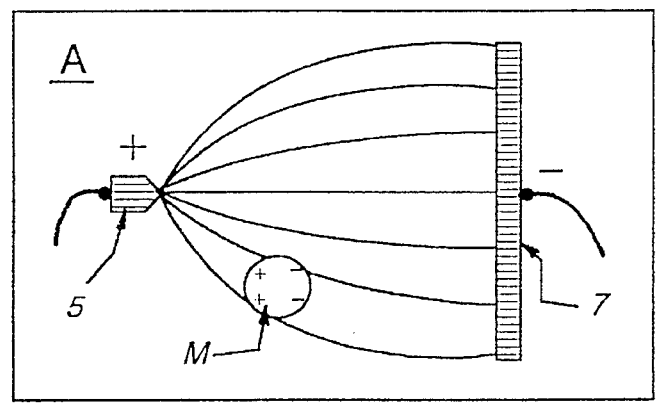
FIG. 2B is a schematic depiction of light scattering due to DLS performed in accordance with the present invention but with the polarity of the field reversed, using the apparatus of FIG. 1.
Figure 3:
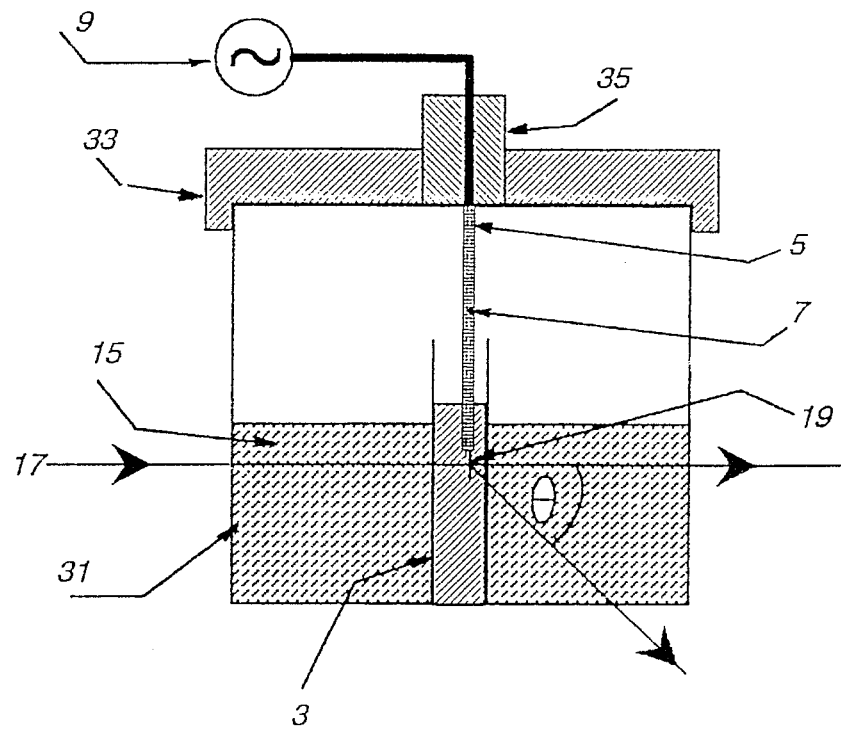
FIG. 3 is a diagram of a sample cell and electrode configuration used in conjunction with the present invention.

The sample cell 3, depicted schematically in FIG. 3, contains the mixture of the macromolecules to be analyzed. Its walls must be transparent to light, and are preferably made of glass or quartz. The cell may be immersed in a bath of index-matching fluid 15 (FIG. 3) to minimize the scattering of the laser beam 17 at the glass-air interface. The electrodes 5 and 7 are comprised of noble metal, such as platinum and may be shielded by a suitable insulator, leaving only the tips 19 unshielded. The edge of one of the electrodes is displaced from the edge of the other electrode so as to create a non-uniform field, as depicted in FIG. 2. The electrodes are immersed into the sample cell and aligned so that a part of the incident light beam hits an electrode to create a heterodyne mode. The RF source 9 provides the electric power needed for an electric field and field gradient generation, and may be amplified by using a broad-band RF amplifier. The light source provides a coherent (laser) beam 17 at a wavelength suitable for the mixture to be analyzed, so that components in the mixture do not absorb the light and produce heat. The optics consist of lenses 21 (FIG. 4) to focus the beam into a small area in the sample cell and to convey the scattered light 23 to the detection system 11.

The detection system comprises of a photomultiplier tube 11 or a photon counter, an analog-to-digital converter 25 to convert the light pulses into digitized input, a correlator 13 which uses the digitized input to calculate the time autocorrelation function, $C(\tau)$, described above, which can be stored using a computer 27, and analyzed on-line or thereafter.

The procedure for the measurements is affected by immersing the electrodes in the sample cell 3 containing the solution under study. The sample cell may be surrounded by a bath of refractive index-matching fluid 15, which may be used to also control the temperature. An oscillation electrical signal (typically sinusoidal) from a function generator is amplified through a broad-band RF amplifier and fed to the two electrodes 5 and 7. The field gradient is achieved by alignment of the two platinum electrodes so that their edges are displaced from each other (as best seen in FIG. 3), resulting in a non-uniform field. A laser beam 17 (e.g. an Argon ion or a He-Ne laser) impinges on the solution in sample cell 3. The laser beam also impinges on the uninsulated tip 19 of the electrode 5 to generate a heterodyne dynamic light scattering mode as discussed above. A DLS spectrum may be collected with no applied field to determine the parameters obtainable from the normal DLS measurements (diffusion coefficient, hydrodynamic radius). The field is turned on and a frequency of the RF field is selected. Measurements in the presence of the field are then recorded. The field strength and gradient, the field frequency, and the scattering angle may be adjusted to achieve the desirable effect on the dispersion under study.

Analysis of data may be performed by the Fourier transform as follows: The component of the spectrum due to the Brownian motion is removed to avoid artifacts in the Fourier transform, as the Brownian motion of the macromolecules present will be superimposed by the motion under the dielectrophoretic effect. This may be accomplished by curve-fitting the $C'(\tau)$ to an exponential function since DLS autocorrelation functions from Brownian and other random motions are exponential. This exponential fit is subtracted from subsequent $C'(\tau)$ to give the oscillations due to the dielectrophoretic effect. A Fourier transform is then performed on the pure oscillations. The peaks in the transform (v space) may be assigned to species present in the dispersion. The velocities in the Fourier transform may be normalized (using the applied field strength and gradient) to assign specific velocities (mobilities) for the species.

ADVANTAGES OF INVENTION

The present invention offers a new method for studying particulate matter in solution, with distinct advantages, including:

i. High sensitivity measurements for biological cell suspensions: For biological cells, their apparent high dielectric constants would prove advantageous to producing large signals. The present invention will furnish a 'signature' to characterize 'normal' or 'healthy' populations in cases of polymers or biological cells, respectively.

ii. Applicability to neutral populations, providing a greater leverage in characterizing mixed populations of a large class of macromolecules. Macromolecules that are neutral (but polarizable) will still experience motion under the field. This method may be used to resolve neutral particle distributions and biological cells at their isoelectric points.

iii. The frequency dependence of the dielectrophoretic mobility provides an important variable in the present invention The frequency of the applied field may be used to selectively enhance the mobility of certain populations in solution mixtures. Biological cells show some characteristic response to the field frequency. It has been shown that some cells respond specifically to certain frequencies of the field, experiencing greater effect from the field at those frequencies. Since the state of a normal biological cell corresponds to a certain configuration of charges inside and on the cell surface, the present invention can be used to probe a biological cell and indicate changes in its state.

iv. The present invention furnishes a fast means (seconds to minutes) to study dielectrophoretic behavior.

v. Resolution improvement: DLS has limited resolving power of components in solution due to the strong overlap of the autocorrelation functions as discussed earlier. The enhancement of the resolving power is due to adding structure to the composite autocorrelation functions. There are at least three factors that contribute to resolution in the present invention: First, the difference in the dielectric constant of the species present, as apparent from Equations 5 and 6. As mentioned earlier, this effect would be particularly pronounced for biological cells. Studies on live and dead cells have shown that the two populations are affected differently by dielectrophoresis. Second, the difference in volume between the species present as indicated by Equation 3. In Example 2 below, measurements indicate that neutral latex particles 2.9µ and 4.1µ in diameters can be easily identified. Third, the frequency of the applied field. As indicated from earlier discussion, depending on the mechanism of polarizability, different populations would 'resonate' with specific frequencies.

vi. Low heat evolution, as no or insignificant electrolysis would occur, as the electrodes can be isolated from contact with solutions.

vii. Elimination of electrolysis gas bubbles and electrodic polarization, due to the use of high frequency oscillating fields.

A potential limitation is a clustering of particles or cells, called 'pearl chain formation' which occurs when the field strength is larger than a certain threshold value. Pearl chains can potentially complicate the interpretation of the results, as they may form their own peaks in the Fourier transform. The chains are large and their formation time is usually longer than the measurement time. Since they are large, they are susceptible to precipitation. The formation of pearl chains may be avoided altogether by applying a field lower than the threshold value which is required for their formation. Another limitation in biological cell suspensions may arise due to the high conductivity of the solution, which may cause heat generation. This may be remedied by the use of certain buffers, electrodes, insulation and geometry.

Figure 1:
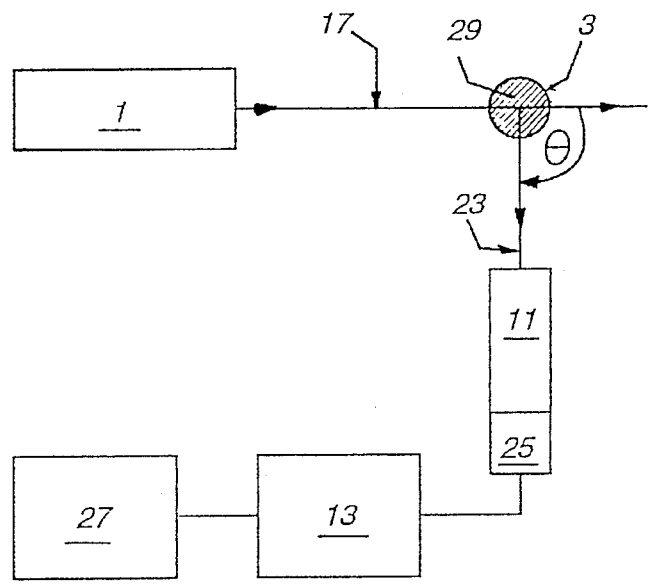
FIG. 1 is a block diagram of the apparatus used for carrying out dynamic light scattering (DLS) in accordance with the invention.

In referring to the drawings, FIG. 1 is a schematic depiction of a dynamic light scattering spectrometer, which consists of a laser light source 1 that provides a coherent beam 17. The beam 17 enters a sample cell 3 which contains a sample 29 to be analyzed. Scattered light 23 at an angle θ leaves the cell 3 and enters a photomultiplier tube 11. The photomultiplier 11 converts the scattered light 23 into voltage pulses. The voltage pulses are transferred to an analog-to-digital (A–D) converter 25 used by a digital correlator 13. The A–D converter 25 converts the voltage pulses into digital output and the digital correlator 13 uses the digital output to calculate the time autocorrelation function $C(\tau)$. The result of the autocorrelation is stored in a computer 27 where the data may be displayed and analyzed.

FIG. 2 diagramatically shows the dielectrophoretic effect when an electrical field, represented by the curved lines, is made to be non-uniform by virtue of the configuration of the electrodes, 5 and 7. In the top panel A a neutral but polarizable macromolecule M is subjected to the field which polarizes the macromolecule and subjects the macromolecule to experience a higher force on its end facing the negative electrode. This forces the macromolecule toward the cathode. Upon a reversal of the polarity of the field, as shown in the lower panel B, the macromolecule M will experience a similar effect, but will not change its direction of motion albeit the reversal in the polarity of the applied field.

The configuration of the sample cell 3 and electrodes 5 and 7 are shown in FIG. 3. The sample cell includes a sample holder made of transparent material which, in turn, is placed in another clear container 31. The container 31 is preferably filled with an index-matching fluid 15 and is covered with an insulating cover 33. The cover 33 also serves to support the insertion of two insulated platinum electrodes 5 and 7. The electrodes 5 and 7 are connected via a connector 35 to a source 9 of an oscillating electrical voltage, which is conducted to the solution via the uninsulated tips 19 of the electrodes, which are of different lengths to generate a non-uniform field. The incident light beam 17 partially hits the uninsulated tip 19 of one of the electrodes to create heterodyne effect. Scattered light 23, at an angle θ, can be collected and analyzed as in FIG. 1.

FIG. 4 schematically shows the configuration of a device to carry out the identification of macromolecules and biological cells based on their dielectrical properties according to the present invention. The device includes a laser light source 1 which emits a beam 17. The laser beam 17 is passed through a focusing lens 21 and into the sample solution, contained in a sample cell 3 made of transparent material. The sample cell 3 is placed in another clear container 31 which may be filled with an index-matching fluid 15 and covered with an insulating cover 33. The cover 33 also serves to support the insertion of two insulated platinum electrodes 5 and 7 which have uninsulated tips 19. The electrodes 5 and 7 are connected via a connector 35 to a source 9 of oscillating electrical voltage, which is conducted to the sample solution via the uninsulated tips of the electrodes. The electrode tips are of different lengths to generate a non-uniform field when the light beam 17 impinges on the electrode tips. Where the incident light beam 17 partially hits the uninsulated tip 19 of one of the electrodes a heterodyne effect is created and scattered light 23 exits sample cell 3 at an angle θ from the emitted beam 17.

The scattered light 23 enters a photomultiplier tube 11 which converts the scattered light into voltage pulses. The output from the photomultiplier tube 11 is received by an analog-to-digital (A–D) converter 25 which converts the signal from the photomultiplier tube 11 into a digital output. The digital output from the A–D converter 25 is received by a digital correlator 13 which then calculates the time autocorrelation functions $C(\tau)$ and $C'(\tau)$. The data from the autocorrelation functions are then stored in a computer 27 where the data may be analyzed and displayed.

Figure 5:
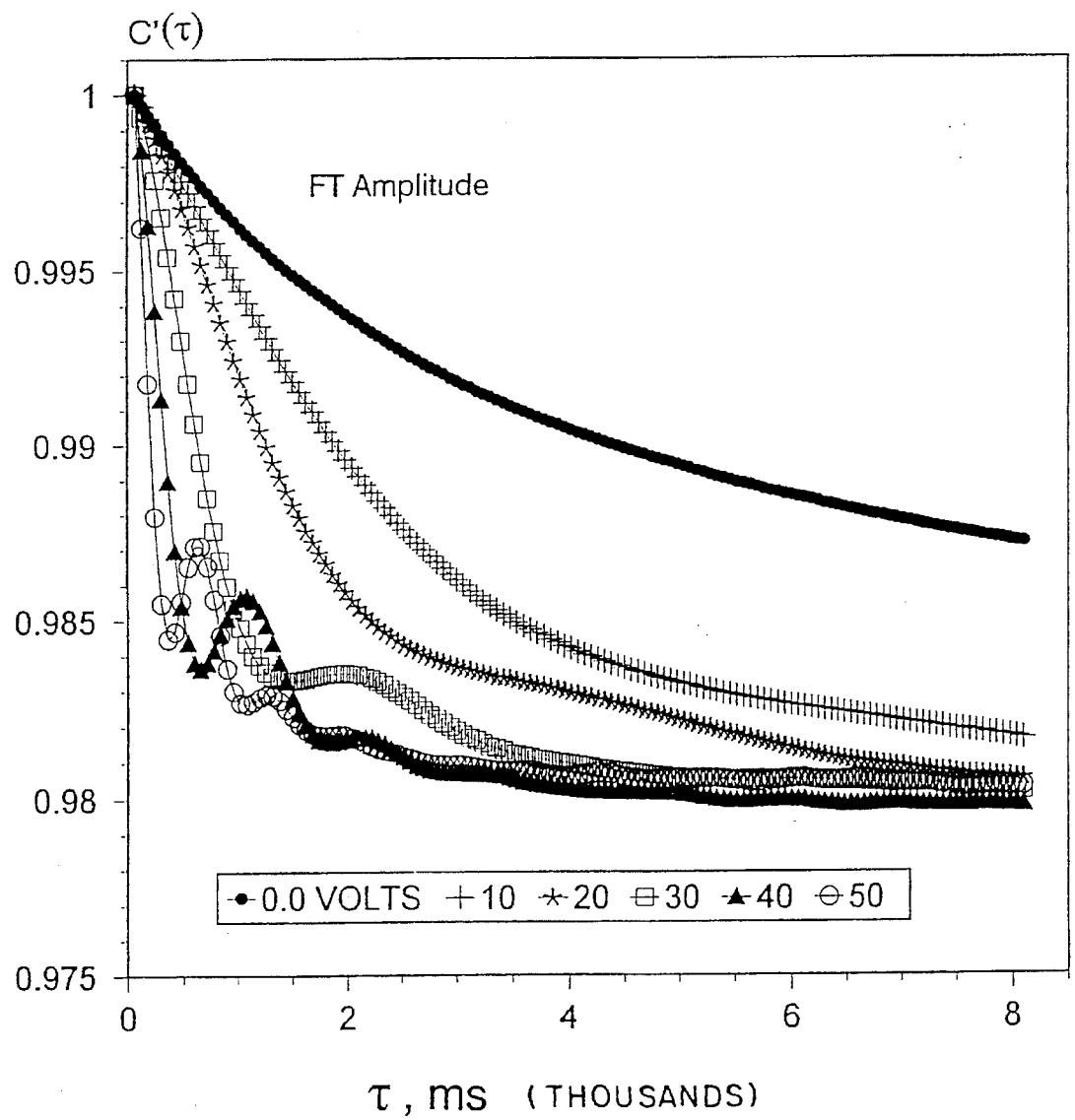
FIG. 5 is a graph plotting the autocorrelation function, $C(\tau)$, for DLS performed in accordance with the present invention on an 0.98 micron latex sample.

FIG. 5 is a chart which plots the autocorrelation function $C'(\tau)$ against time shift $\tau$ for different voltages which are applied to a $2\times10^{-6}$ gram/ml sample of 0.98 micron latex sample obtained from Polyscience Corporation. The scattering angle $\theta$ was at 90°, the sample temperature was 23°C, and the laser beam 26 was produced by an Argon ion laser operating at 488 nm. The graph of FIG. 5 plots the auto- correlation function against time with various voltages (0V to 50V) being passed through the electrodes. The frequency of the oscillating sinusoidal field was 350 kHz frequency. The inset (FIG. 5A) plots the Fourier transform of the data from FIG. 5, and shows a predominant single peak representing the velocity of the 0.98micron latex particles under the field.

Figure 6:
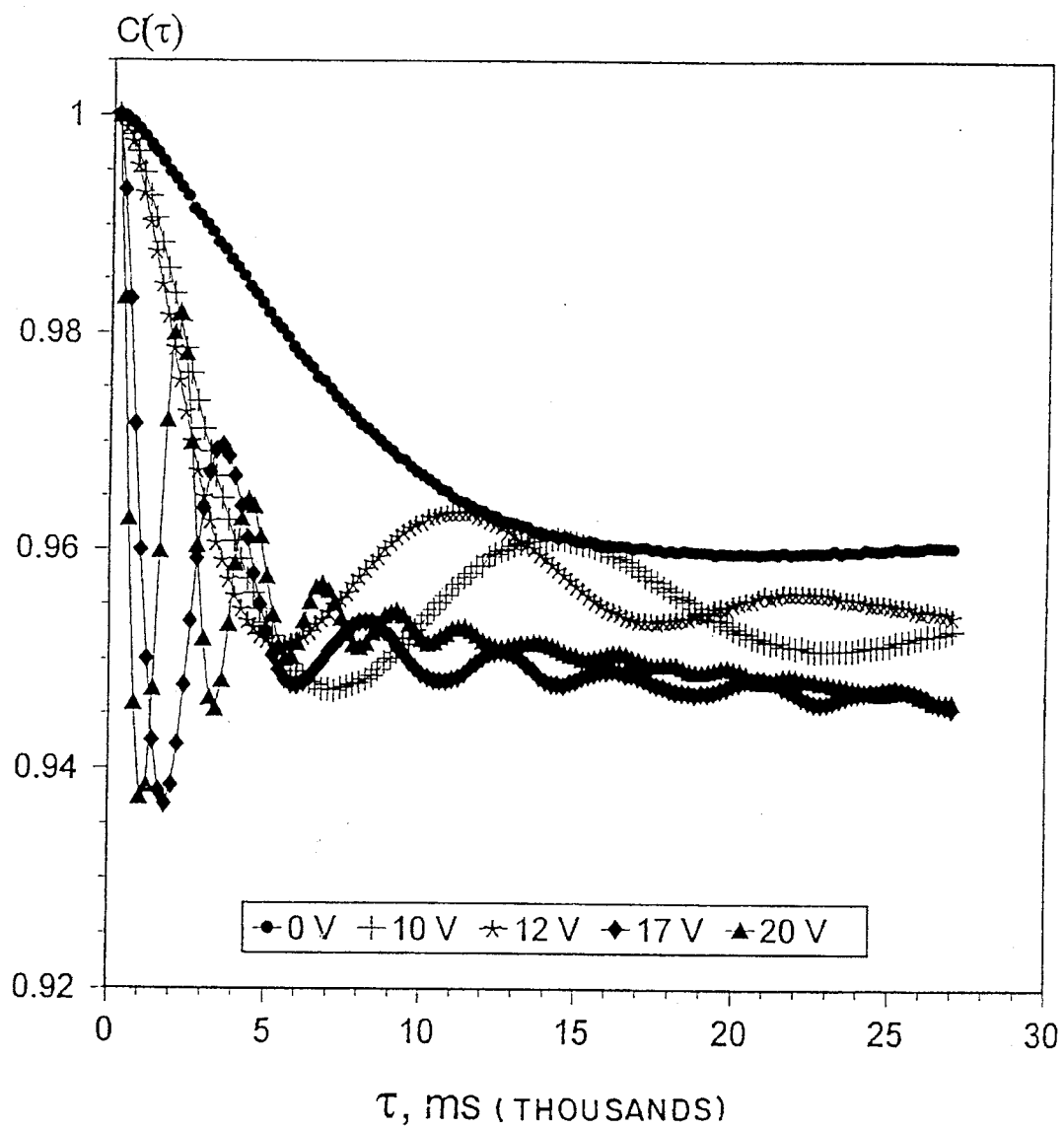
FIG. 6 is a graph similar to FIG. 5 for showing a 4.1µ latex sample.
Figure 6A:
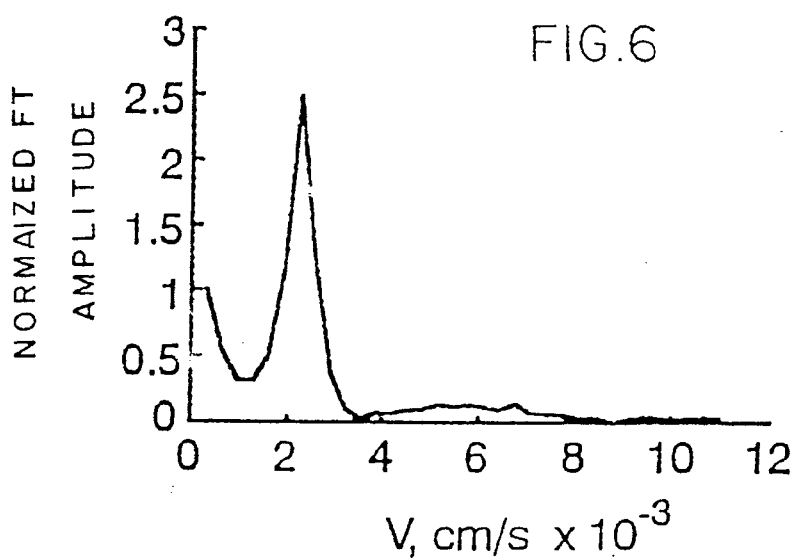
FIG. 6A is a graph plotting the Fourier transform for the data of FIG. 6.

FIG. 6 is a graph similar to the graph of FIG. 5 of the autocorrelation function $C'(\tau)$ against time for dielectrophoretic DLS on 4.1 micron latex sample using the device of FIGS. 2 and 4. The inset (FIG. 6A) shows the Fourier transform of the data. The graph of FIG. 6A shows a predominant single peak representing the velocity of the particles under the field.

Figure 7:
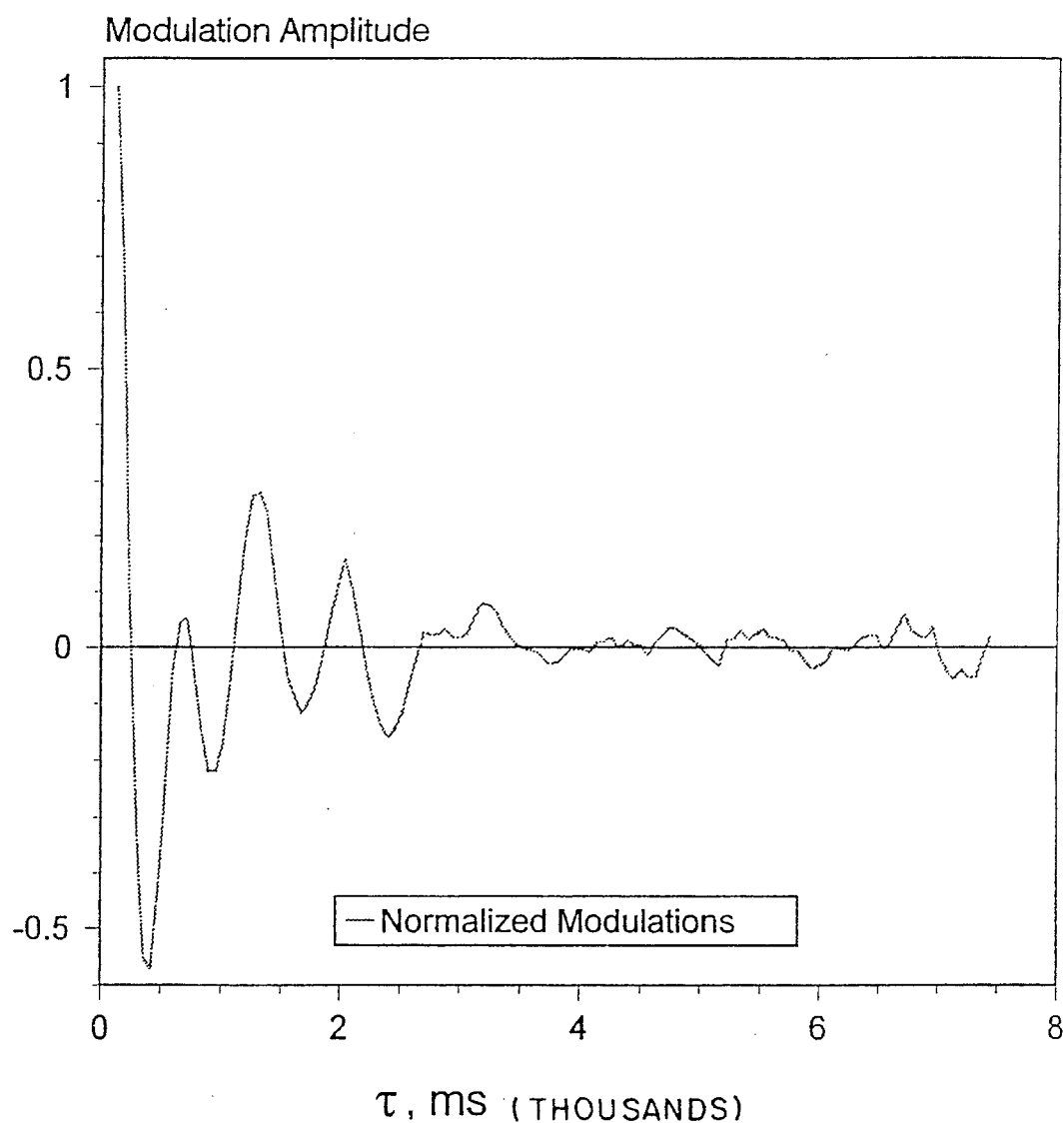
FIG. 7 is a graph similar to FIG. 5 for a polydiverse system containing 4.1 and 2.98 micron latex.
Figure 7A:
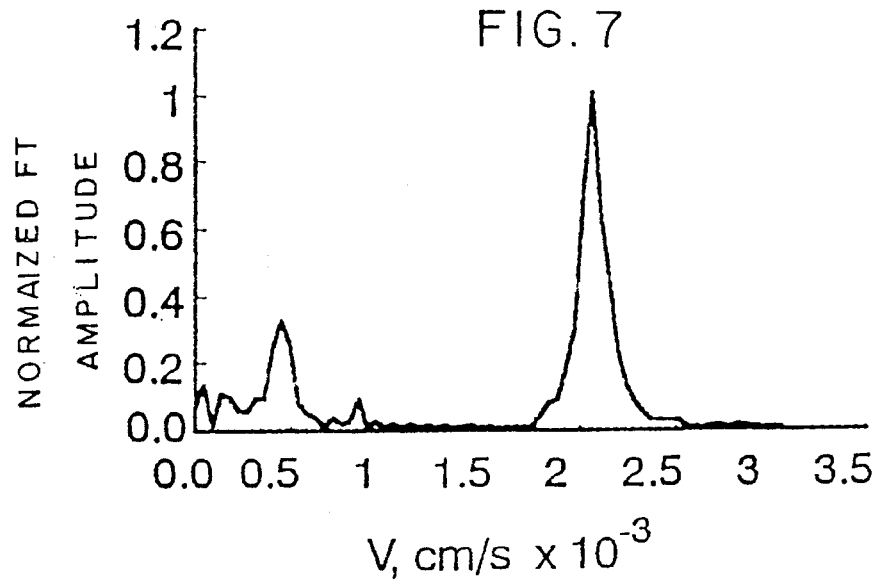
FIG. 7A is a graph plotting the Fourier transform for the data of FIG. 7.

FIG. 7 is a graph showing data on a mixture of 4.1μ and 2.98μ latex samples which were diluted to $2\times10^{-5}$ gram/mi. The remaining conditions were similar to those of Example I. The device of FIGS. 3 and 4 was used under a field of 50 volt/cm. The data collected was treated by removing the component due to the Brownian motion by fitting the data to a single exponential, and subtracting the fit from $C'(\tau)$ to yield only the oscillations due to the field effect. The results of the Fourier transform are displayed in the inset (FIG. 7A). The Fourier transform shows two predominant peaks representing the two populations of particles present.

FIG. 8 graphs the autocorrelation function against $\tau$ for dielectrophoretic DLS carried out on a Baker's yeast cell suspension using the device of FIG. 4 under the conditions of example below. The sample was diluted to $2\times10^{-3}$ % solid, using the device described in FIG. 4 and Example 4, with other conditions being similar to those in FIG. 5. The inset (FIG. 8A) shows the Fourier transform of the data. The Fourier transform produced a multiplicity of peaks which are stipulated to represent the velocity of the different species of yeast cells under the field.

EXAMPLE 1

Figure 5A:
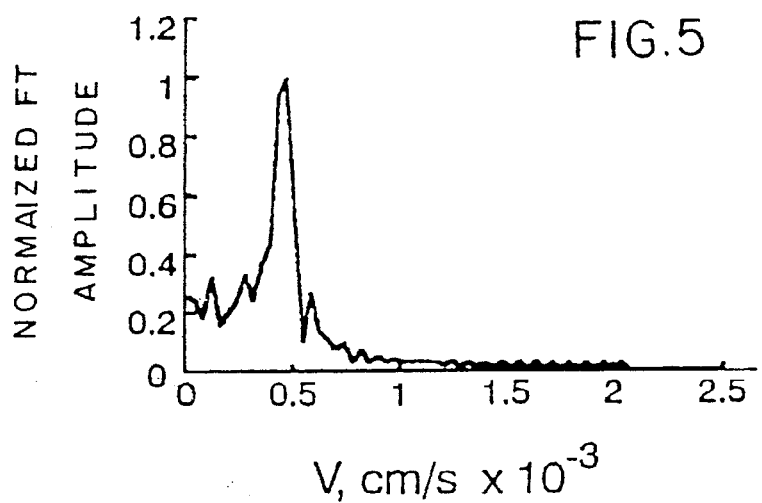
FIG. 5A is a graph plotting the Fourier transform for the data of FIG. 5.

A sample of 0.98 micron latex particles, obtained from Polyscience Corporation, was diluted to a $2\times10^{-6}$ gram/ml concentration with distilled water. The sample was placed in the sample cell, as described in FIG. 4. The sample cell was placed in another glass container which was filled with fluid possessing a refractive index matching that of glass fluid container. A hole drilled in the cover served as a support of two insulated platinum electrodes. The electrodes were connected to the output of an electrical wave generator after amplification using a broad-band radio frequency amplifier. The tips of the electrodes were uninsulated and were placed staggered (different lengths) to generate a non-uniform field. An argon ion laser provided a beam at 448 nm which was focused on the sample using lens. The. beam was positioned to partially impinge on the uninsulated tip of one of the electrodes to create a heterodyne effect. Scattered light at 90° was collected via a photomultiplier and was converted into digital output using an analog-to-digital converter. A digital correlator was used to calculate the time autocorrelation functions. The data were analyzed using a personal computer. The normalized heterodyne autocorrelation functions am displayed in FIG. 5. The top curve shows the function with no field application (i.e. 0V), while the lower oscillating curves show the effect of the application of a 350 kHz, with varying strength, as noted in FIG. 5. The number of oscillations increased with increasing field strength, as predicted by Equation 8. The analysis was performed on the autocorrelation function collected with the application of 80 volts/cm field. The analysis was performed after removing the component corresponding to the and was accomplished by fitting $C(\tau)$ to a single exponential and subtraction the fit from $C'(\tau)$. A predominant single peak representing the velocity of the 0.98 micron latex particles under the filed is displayed in the inset (FIG. 5A). A single peak is predicted since the sample contains mainly monosized particles.

EXAMPLE 2

A sample of 4.1 micron latex particles was diluted to a $1\times10^{-6}$ gram/ml concentration. Data were collected and analyzed using conditions similar to those described in Example 1. FIG. 6 presents the data with no application of electrical field (i.e. 0V) in the top curve, and with the application of field with different intensities in the remaining curves. The inset (FIG. 6A) to FIG. 6 represents the Fourier transform of data, carried out as described in Example 1, and shows a predominant single peak representing the velocity of the 4.1 micron latex particles under the field.

EXAMPLE 3

A mixture of 2.98 and 4.1 micron latex beads (Polyscience) were prepared at a 1:1 ratio to give a final concentration of $2\times10^{-5}$ gram/ml in each component. Measurements and analysis were carried out on the mixture as explained in Example 1. FIG. 7 shows the resulting normalized spectra from the mixture. Preliminary Fourier transform shows two distinct peaks in velocity domain, shown in the inset (FIG. 7A) to FIG. 7. The peaks represent the velocity of the 2.98 and 4.1 micron latex particles under the field.

EXAMPLE 4

Figure 8A:
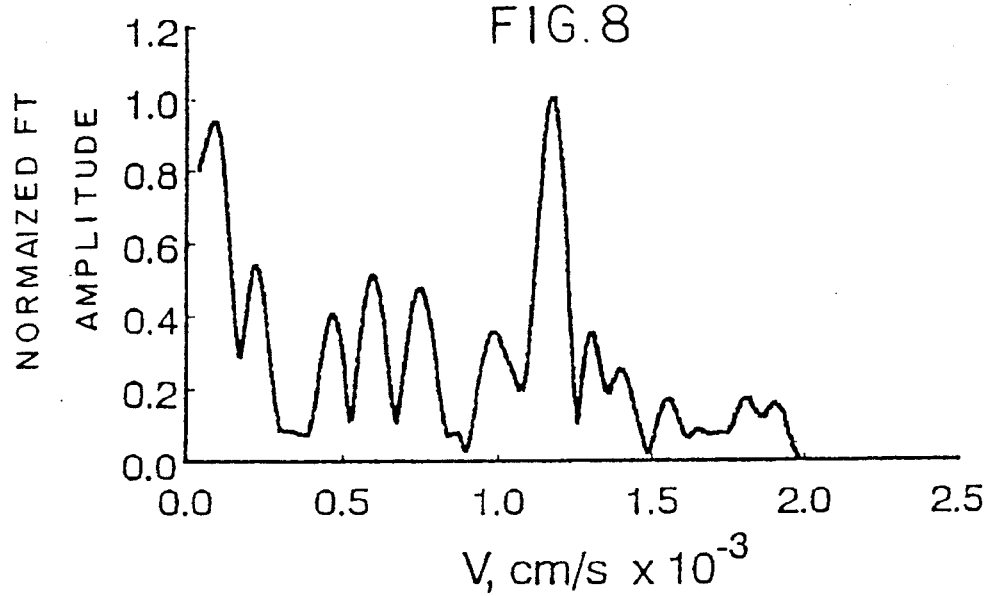

A 0.5 gram sample of baker's yeast was suspended in 100 ml water. Measurement was carded out as explained in Example 1. FIG. 8 shows the resulting spectrum from the mixture collected at 80 Volts/cm of applied field. Analyzing the data as explained in Example 1 shows numerous peaks in velocity domain (FIG. 8A).

The resolution enhancement of the peaks in discovering these populations would not be possible without the application of the non-uniform field as described in this invention. The multiplicity of peaks are stipulated to represent the velocity of the different species of yeast cells under the field.

The foregoing summary, description and drawing, and description of the preferred embodiments, in addition to a variety of examples that define the use and application of this invention, have been previously reviewed. Variation or modifications to the subject matter of this invention, may be envisioned by those skilled in the art. Such variations or modifications, if within the spirit of this invention, are intended to be encompassed within the scope of any claims to patent protection issuing upon this development. The description as set forth herein is done so for illustration purposes only.

Having thus described the invention, what is claimed and desired to be secured by Letters Patent is:

1. A device for the detection and analysis of populations of neutral or electrically-charged solutes that are polar or polarizable, such as large molecules, polymers, biological cells, and particulate matter in a fluid solution; said device including:
   a) two electrodes configured such that upon applying an electric potential, an electric field gradient is created between the two electrodes;
   b) an electric field generator connected to said electrodes, which can produce an oscillating electric signal that can polarize the solutes in the solution, said electric signal of frequency from 0 to 1000 million hertz;
   c) a vessel which contains a sample solution to be analyzed, and wherein said electrodes are immersed, said vessel being made of transparent material;
   d) a coherent light source for producing a highly collimated light beam, said light beam impacts on the sample solution, thereby producing scattered light off the sample solution at a given angle, said light beam is directed to partially impinge on one of the electrodes to create a heterodyne effect;
   e) a photomultiplier or a photon counter for detecting said scattered light, said photomultiplier or photon counter being positioned at said angle, said photomultiplier converting said scattered light into electric signals;
   f) an analog-to-digital converter in communication with said photomultiplier or photon counter, said analog-to-digital converter converting said electric signals output; and
   g) a digital correlator which receives the digital output from said analog-to digital converter to calculate a time autocorrelation function of the motion of the said solutes in said solution.

2. The device of claim 1 wherein said electrical signal has a frequency of between 50,000 and 100 million hertz.

3. The device of claim 1 wherein said electrodes are made of a noble metal.

4. The device of claim 1 wherein said vessel containing said sample solution is made of glass or quartz.

5. The device of claim 1 and wherein said solution vessel is immersed in another clear vessel filled with a fluid whose index of refraction matches that of the solution vessel wall material; whereby scattering of light off the walls of the solution vessel is minimized.

6. The device of claim 1 and wherein said solution vessel is thermostated to keep the solution at a constant temperature during measurement.

7. The device of claim 1 and wherein said oscillating electric signal is strengthened by using an amplifier.

8. The device of claim 1 and wherein said coherent light source is a laser source.

9. The invention in claim 1 and wherein the frequency of said electrical field generator is chosen to correspond to the maximum response under the field gradient of a particular solute, whereby said solute produces an enhanced signal.

10. A method for achieving the detection and analysis of populations of neutralor electrically-charged solutes, such as large molecules, polymers, biological cells, and particulate matter in a fluid solution, said process using the device of claim 1, said method including:
    a) measuring the time-dependent autocorrelation function of said solutes is measured without the application of the electric field to determine C(t);
    b) generating an oscillating electric field gradient at a desired frequency, electric field strength and field gradient strength;
    c) measuring the time-dependent autocorrelation function under the influence of the applied field gradient to determine C'(t);
    d) removing the component of the C'(t) due to the Brownian motion by fitting C'(t) to an exponential function, and whereupon the exponential fit is subtracted from C'(t) to give the pure oscillations due to said field gradient,;
    e) performing a Fourier transform on said oscillations, and whereupon the resulting peaks in said Fourier transform represent the motion of said solutes under the field gradient and said peaks are assigned motion of specific solutes present in the solution; and
    f) normalizing the velocities in said Fourier transform in units of applied field strength and field gradient to assign specific motion, or mobilities, for the scattering solutes, thereby constituting the basis of a new spectral analysis of said solutes.

11. The method of claim 10 and wherein the autocorrelation function is accomplished utilizing an electronic analog scheme.

12. The device of claim 1 wherein the autocorrelation function is accomplished utilizing an electronic analog scheme.

13. The device of claim 1 wherein said fluid solution is substantially non-conductive.

14. The method of claim 10 and wherein said fluid solution is substantially non-conductive.

15. The device of claim 1 and wherein said field gradient is substantial.

16. The method of claim 10 wherein said field gradient is substantial.

* * * * *